United States Patent [19]

Tseo et al.

[11] Patent Number: 4,605,396
[45] Date of Patent: Aug. 12, 1986

[54] GRAVITY FLOW CASSETTE WITH ROTARY VALVE

[75] Inventors: Gus G. Tseo, San Diego; Dennis L. Fitzwater, Murrieta, both of Calif.

[73] Assignee: Warner-Lambert Company, Morris Plains, N.J.

[21] Appl. No.: 704,803

[22] Filed: Feb. 25, 1985

[51] Int. Cl.[4] ............................................. A61M 1/00
[52] U.S. Cl. ............................ 604/32; 128/DIG. 12; 604/152
[58] Field of Search .................. 417/418; 137/625.17; 604/31, 32, 65-67, 151-155, 246; 128/DIG. 12, DIG. 13

[56] References Cited

U.S. PATENT DOCUMENTS

| | | | |
|---|---|---|---|
| 3,269,412 | 8/1966 | Badke | 137/625.17 |
| 3,354,910 | 11/1967 | Moen | 137/625.17 |
| 3,985,133 | 10/1976 | Jenkins et al. | 128/214 F |
| 4,047,527 | 9/1977 | Kelsen | 128/229 |
| 4,303,376 | 12/1981 | Siekmann | 417/518 |
| 4,396,385 | 8/1983 | Kelly et al. | 604/152 |
| 4,423,741 | 1/1984 | Levy | 128/768 |
| 4,450,079 | 5/1984 | Farr | 604/152 |

Primary Examiner—C. Fred Rosenbaum
Assistant Examiner—J. L. Kruter
Attorney, Agent, or Firm—Neil K. Nydegger

[57] ABSTRACT

A gravity flow cassette for use with an I.V. infusion pump has a fluid inlet, a fluid outlet and a pump chamber with associated pump piston. A valve body having an annular groove and a partial groove parallel thereto is slidably disposed in the cassette for reciprocal movement between a first position and a second position. Engagement of the cassette with the pump firmly holds the valve body in the first position wherein the annular groove is sealed and the valve body can be rotated to alternately provide fluid communication through the partial groove between the inlet and the pump chamber or between the pump chamber and the outlet. Upon disengagement of the cassette from the pump, the valve body can be moved into the second position to seal the partial groove and provide for simultaneous fluid communication through the annular groove between the input, the output and the pump chamber.

17 Claims, 11 Drawing Figures

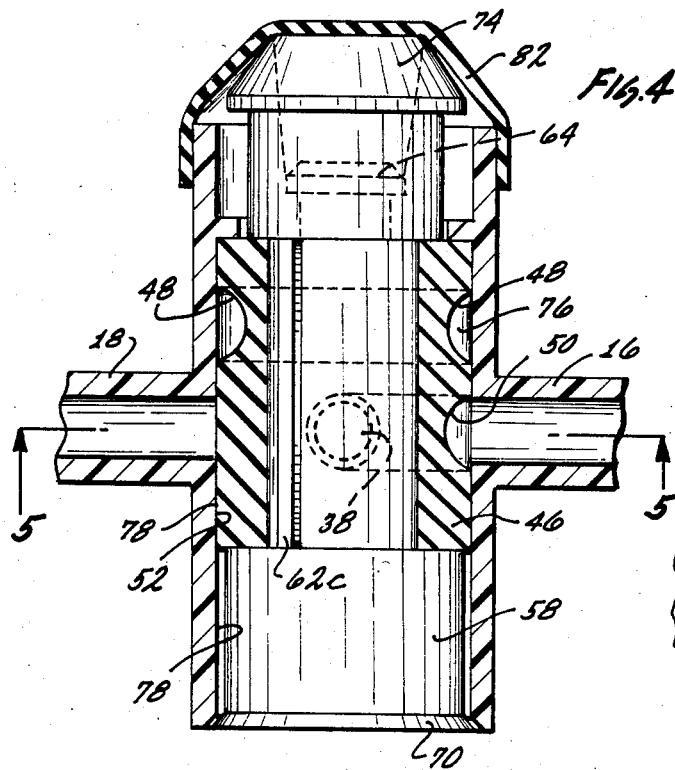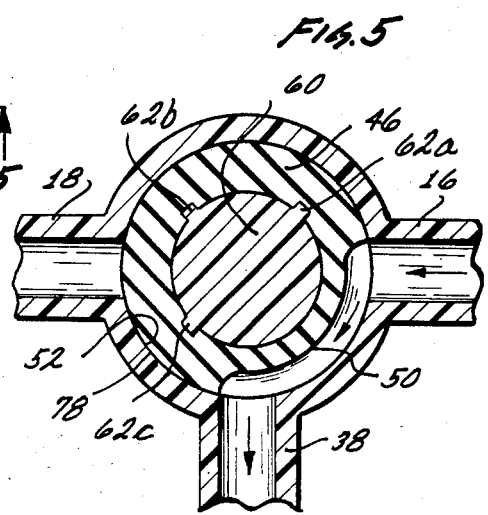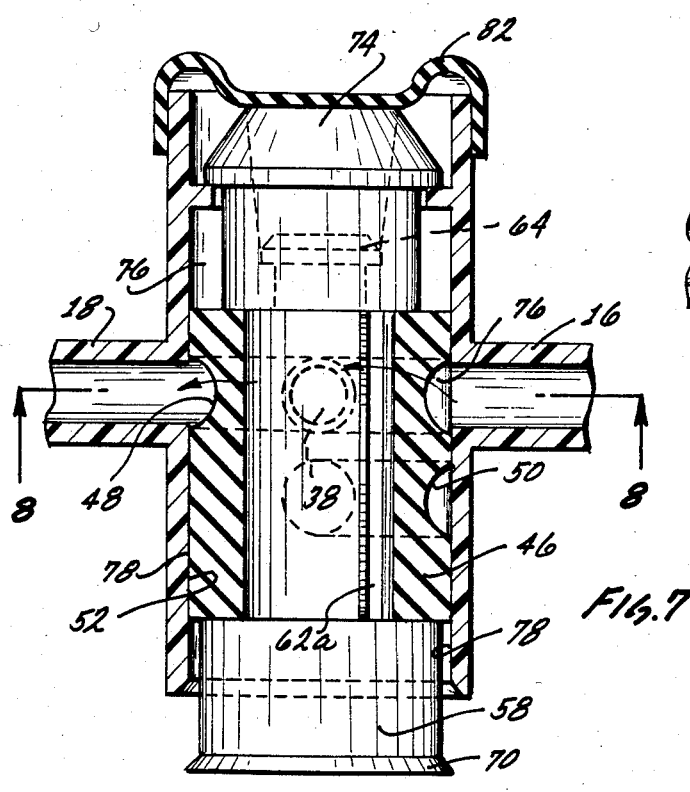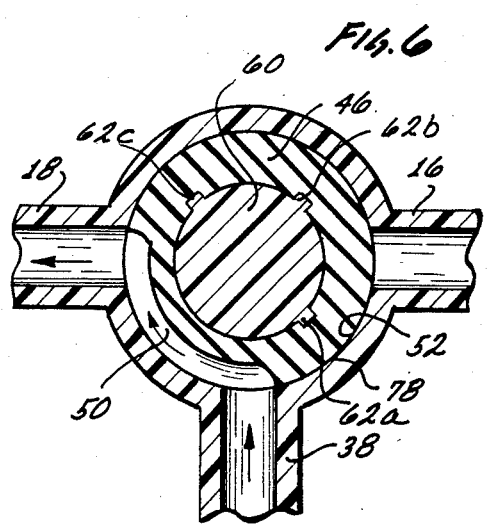

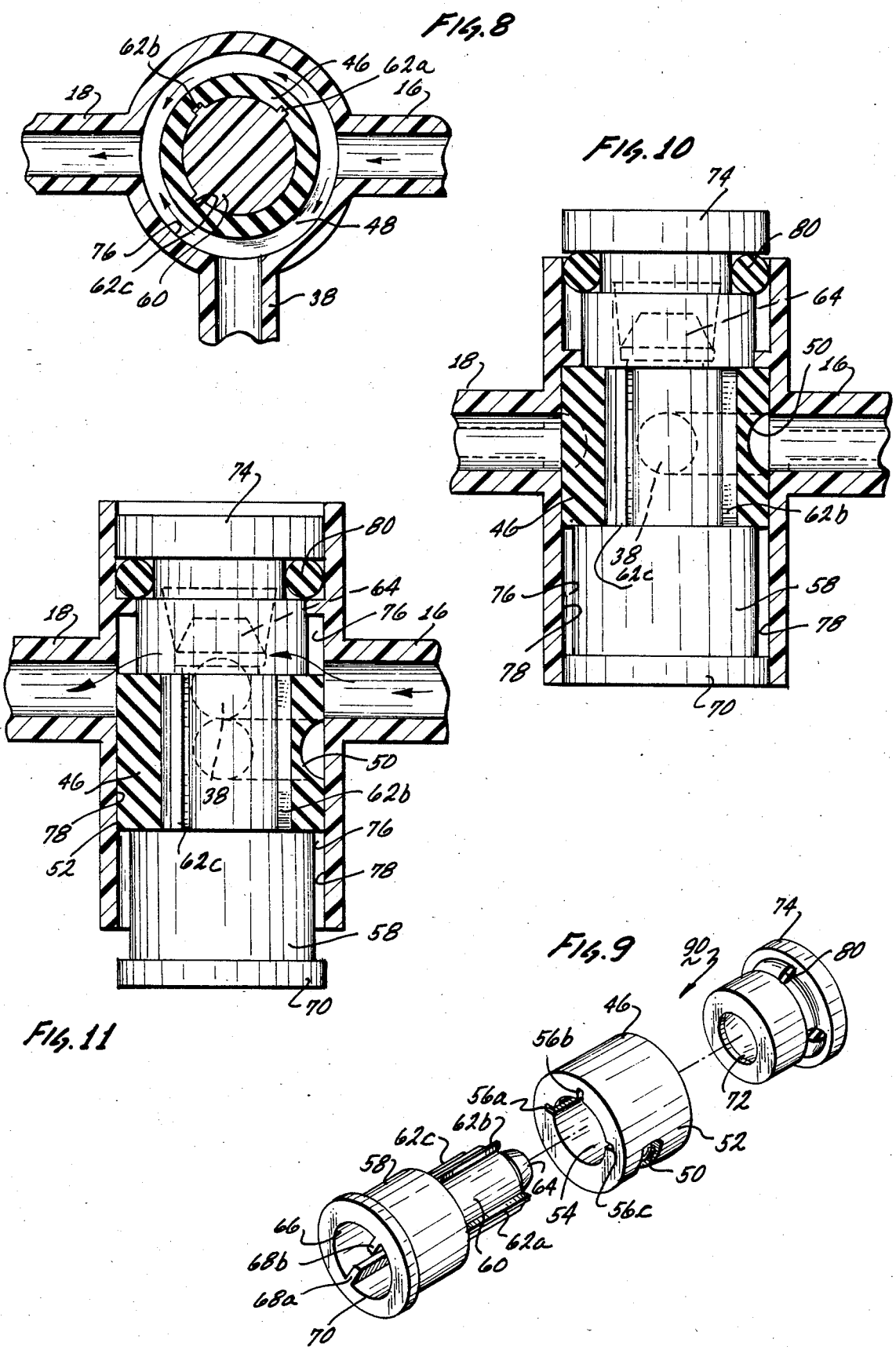

GRAVITY FLOW CASSETTE WITH ROTARY VALVE

FIELD OF THE INVENTION

This invention relates generally to disposable pumping chamber cassettes which are used with an actuator pump drive mechanism. Specifically, the present invention relates to a cassette defining a pumping chamber, a fluid inlet, a fluid outlet and a valve mechanism. During normal pumping operations, the cassette provides sequential valving for fluid communication between the inlet and the pumping chamber to fill the chamber and fluid communication between the pumping chamber and the outlet to empty the chamber. More particularly, the present invention relates to an improvement in the valve mechanism for such a cassette which permits the free flow of fluid between the inlet and the outlet when the cassette is disengaged from the pumping mechanism. This invention is particularly, though not exclusively, useful in conjunction with a pump used for the infusion of I.V. fluids to a patient.

BACKGROUND OF THE INVENTION

Pumps are commonly used in I.V. therapy for the administration of I.V. fluids to a patient. The use of pumps, however, can pose problems when it becomes necessary or desirable to move the patient. These problems are particularly apparent when the pumps are sophisticated, relatively cumbersome, and require extensive peripheral apparatus. Unlike the simple I.V. bottle administration set which allows a patient to move from one location to another with relative ease, when a pump is used for I.V. administration, the cumberous nature of the apparatus can effectively inhibit mobility of the patient.

The problem is aggravated by the fact that typical I.V. systems which use a piston type pump do not provide for disengagement of the fluid line from the pump to leave the fluid line patent between the source and the patient. Instead, such systems usually incorporate a valving device which either fills the pumping chamber or pumps fluid from the pumping chamber. In each of these configurations, the valve does not allow direct fluid flow from the fluid source to the patient. Several examples of this type of I.V. pump and associated disposable pump chamber cassettes are available. Specifically, U.S. Pat. No. 3,985,133 to Jenkins et al., U.S. Pat. No. 4,423,741 to Levy and U.S. Pat. No. 4,450,079 to Farr disclose pump chamber cassettes for I.V. pumping devices which do not contemplate a patent fluid line between the fluid source and the patient.

In order to improve the flexibility of an I.V. pump administration system, there is a recognized need for the capability to disconnect the fluid line from the pumping mechanism for periods of time without breaking into the fluid line or interrupting infusion. Furthermore, there is a need to maintain the integrity of the fluid line during disengagement from the pump to prevent the admission of air into the I.V. system and prevent bacterial contamination of fluids. Several situations can be envisioned where the ability to remove the fluid line from a pumping mechanism would be desirable. For example, there is always the potential need to move the patient unencumbered by the pumping mechanism itself. Further, there may be situations when it is necessary to administer fluid to a patient at a rate faster than is possible by the pumping system, such as would be the case with a burn victim where up to 3 liters of fluid per hour may be required. Also, there are instances when the pumping mechanism may become inoperative and it is desirable to continue the uninterrupted infusion of fluids to the patient during repair or replacement of the pump.

Several fluid flow valving mechanisms have been suggested in the prior art. Of these, some valving mechanisms have been suggested which permit the mixing of fluids from several sources or the redirection of fluid from one source to another. More specifically, fluid valves have been suggested which accomplish these functions by incorporating a slidable and rotatable cylinder in operative association with a housing having various fluid inlet and fluid outlet ports. For example, U.S. Pat. No. 3,269,412 to Badke and U.S. Pat. No. 4,423,741 to Levy disclose reciprocating piston valves having various fluid paths defined therein which are oriented with fluid inlets and outlets to define particular fluid paths through the device. These references, however, do not teach or suggest a cassette pump valve which is restrained to provide for normal valving during the pumping operation and which, upon disengagement of the cassette from the pump, can be repositioned within the cassette to provide for the gravity flow of fluid therethrough.

It is an object of the present invention to provide a means for disengaging an I.V. fluid line from a pumping means without interrupting the administration of fluids to the patient. It is another object of the present invention to allow for such disengagement without the admission of air into the fluid line and without contaminating the fluid being administered to the patient. It is yet another object of the present invention to provide a mechanism which easily converts an I.V. fluid pumping system to a gravity flow I.V. system. Additionally, it is an object of the present invention to provide an inexpensive, easily manufactured and simple to operate device which improves the flexibility of an I.V. administration system.

SUMMARY OF THE INVENTION

A preferred embodiment of the present invention includes a cassette for use with an I.V. infusion pump which comprises a housing formed with a well which is in fluid communication with an inlet port, an outlet port and a pump port extending from the well into the pumping chamber of the cassette. The cassette also includes a cylindrically shaped valve body having a circumferential annular groove formed on the lateral surface or wall of the cylinder and a partial groove substantially parallel to the annular groove and axially spaced along the surface of the cylinder therefrom. The valve body is disposed in the well of the cassette and can be reciprocated and rotated therein. During engagement of the cassette with a pumping mechanism, the valve body is positioned within the well to provide for fluid communication between the pump port and the partial groove. Also, while the cassette is engaged with the pump, means associated with the valve body are operatively engageable with the drive mechanism of the pump to rotate the valve body in the well and alternately provide for fluid communication through the partial groove between the pump port and the inlet or the outlet.

Upon disengagement of the cassette from the pumping mechanism, a button associated with the valve body can be pressed to relocate the valve body in the well and thereby bring the annular groove into alignment with the pump port, the inlet and the outlet. With the annular groove in this alignment, fluid in the I.V. system can flow through the cassette from the inlet to the outlet.

For proper operation of the valve mechanism of the present invention, it is important that the lateral surfaces of the cylindrical shaped valve body be in fluid sealing engagement with the surfaces of the well. Thus, fluid commuication within the well will depend on the positioning of the valve body relative to the inlet, outlet and pump port and can be accomplished only via the annular groove or the partial groove. Importantly, the fluid sealing engagement between the valve body and the well prevents fluid leaks from the cassette during both its engagement with a pumping mechanism and its disengagement therefrom.

The novel features of this invention, as well as the invention itself, will be best understood from the accompanying drawings taken together with the accompanying description in which similar reference characters refer to similar parts and in which:

BRIEF DESCRIPTION OF THE DRAWINGS

FIG. 4 is a top cross-sectional view of the valve body in its association with the well of the gravity flow cassette as seen along the line 4—4 in FIG. 2;

FIG. 5 is an end cross-sectional view of the valve body in the well of the cassette housing as seen along the line 5—5 in FIG. 4;

FIG. 6 is an end cross-sectional view of the valve body as seen in FIG. 5 with the valve body rotated;

FIG. 7 is a top cross-sectional view of the valve body in its association with the well of the cassette showing the valve body displaced from its position as shown in FIG. 4;

FIG. 8 is an end cross-sectional view of the valve body as seen along the line 8—8 in FIG. 7;

FIG. 9 is an exploded perspective view of the valve body and its associated elements for an alternate embodiment of the present invention;

FIG. 10 is a top cross-sectional view of the valve body positioned in the well of the cassette in an alternate embodiment of the present invention; and FIG. 11 is a top cross-sectional view of the valve body located in the well of the cassette in an alternate embodiment of the present invention and displaced from its position as shown in FIG. 10.

DESCRIPTION OF THE PREFERRED EMBODIMENT

Figure 1:
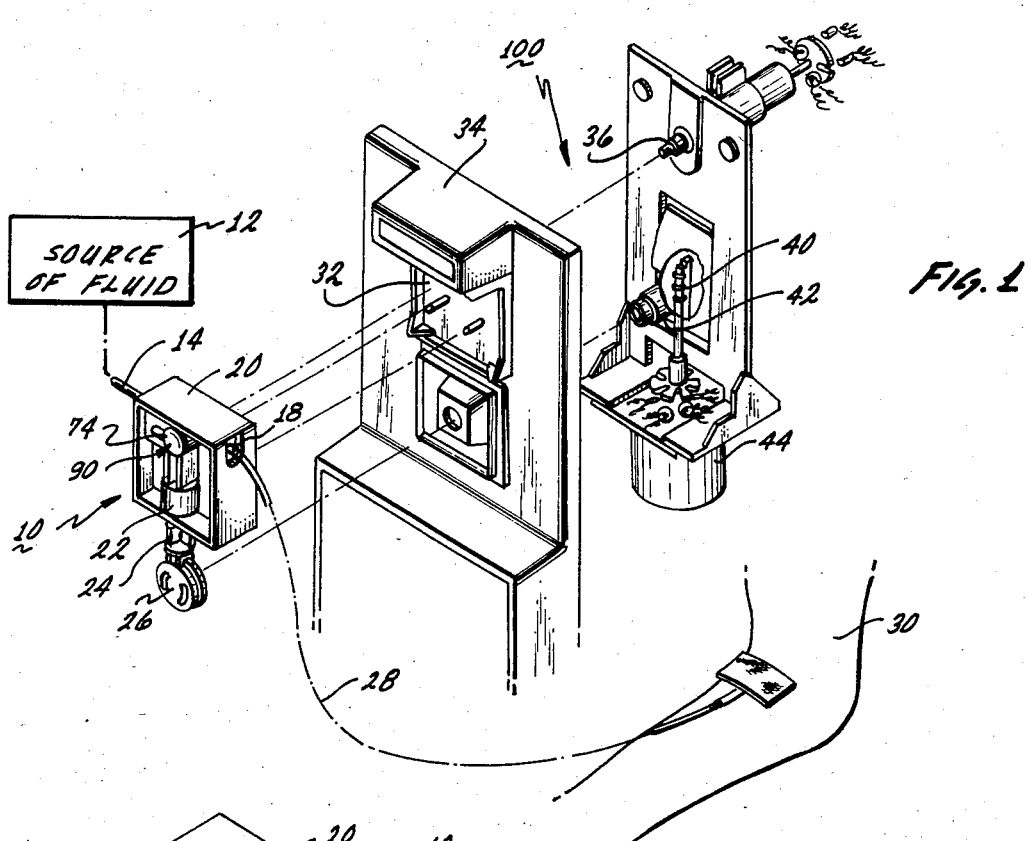
FIG. 1 is a perspective view of the front of the gravity flow cassette and its intended association with a pumping mechanism for the administration of I.V. fluid from a fluid source to a patient.

Referring now in detail to the drawings, the cassette of the present invention is shown in FIG. 1 and generally designated 10. As seen in FIG. 1, the cassette 10 is connected with a fluid source 12 by an inlet line 14 which is engageable with the inlet (not shown in FIG. 1) of cassette 10. Cassette 10 further comprises a housing 20 which is formed with a pump chamber 22. A piston 24 is disposed in pump chamber 22 for reciprocal motion therein to provide a pumping action for fluid flowing through the cassette 10. As also seen in FIG. 1, an outlet 18 is intended for connection with an output line 28 which in turn is connected to a patient 30 for the administration of an I.V. fluid. Still referring to FIG. 1, it is seen that cassette 10 can be associated with a pump, generally designated 100 in FIG. 1. More specifically, cassette 10 is associated with the pump case 34 in a manner that provides flush engagement of the cassette 10 with front plate 32.

Engagement of cassette 10 with pump 100 brings connector 26 into operative connection with shuttle 42 and also brings valving mechanism 90 into operative connection with valve body actuator 36. Stepper motor 44 drives lead screw 40 to reciprocate shuttle 42 and provide for the pumping action of piston 24 in pump chamber 22. Simultaneously with the operation of piston 24, and in coordination therewith, valve body actuator 36 is driven by pump 100 to operate valve mechanism 90 of cassette 10 to direct fluid flow from source 12 into pump chamber 22 and alternately to direct fluid from pump chamber 22 through outlet via line 28 to the patient 30. A more complete description of the intended operation of cassette 10 and pump 100 can be had by reference to U.S. Pat. No. 3,985,133 to Jenkins et al. which is assigned to the assignee of the present invention and which discloses a pump and cassette operation similar to those discussed nere. More specifically, U.S. Pat. No. 3,985,133 discloses a cassette which can be easily modified to incorporate the present invention.

Figure 2:
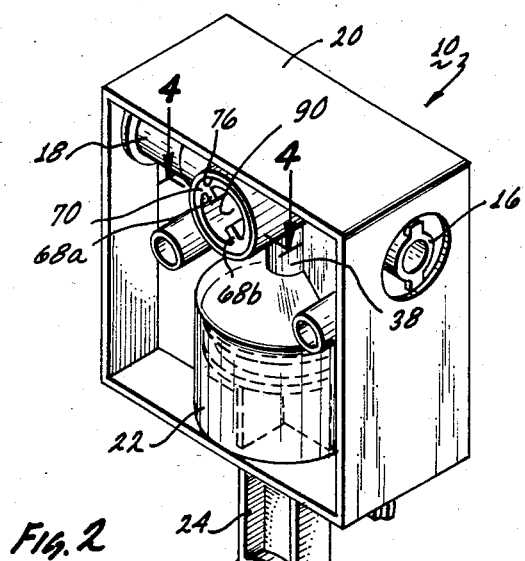
FIG. 2 is a perspective view of the back of the gravity flow cassette shown in FIG. 1.
Figure 3:
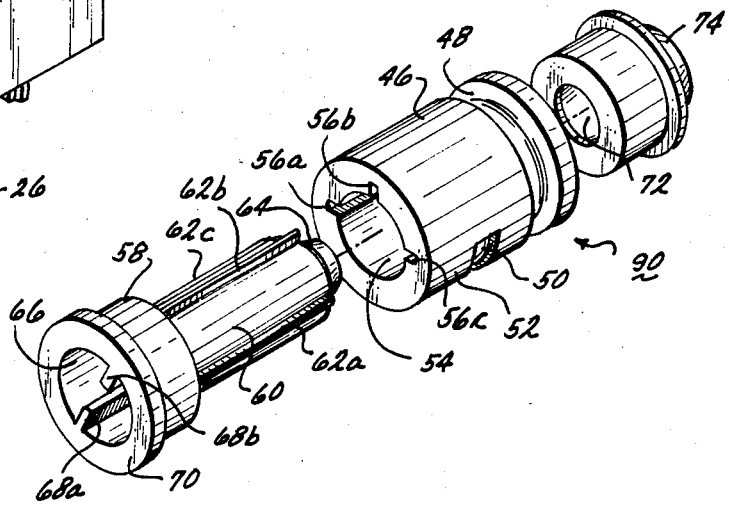
FIG. 3 is an exploded perspective view of the valve body of the gravity flow cassette and its associated elements.

FIGS. 2 and 3 respectively are perspective views of cassette 10 and valve mechanism 90 as seen from the back side of cassette 10 in FIG. 1. Together FIGS. 2 and 3 illustrate the valving mechanism 90 and its association with cassette housing 20. With specific reference to FIG. 3, it can be seen that valving mechanism 90 comprises a valve body 46 which is preferably made of urethane rubber. Formed onto the cylindrical shaped valve body 46 is an annular groove 48 which is located on the surface 52 of valve body 46 and oriented concentrically with the longitudinal axis of valve body 46. An arcuate partial goove 50, which is axially spaced from annular groove 48 and substantially parallel to annular groove 48, is also formed onto the surface 52 of valve body 46.

As seen in FIG. 3, valve body 46 is substantially a hollow cylinder defining an axial bore 54 having radially spaced recesses 56a, b and c therein. An insert 58 having a barrel 60 and splines 62a, b and c disposed longitudinally thereon is adapted to matingly engage with bore 54 of valve body 46 so that splines 62a, b and c are respectively seated into recesses 56a, b and c to allow for simultaneous rotation of the valve body 46 with the insert 58. A shoulder 70 on insert 58 describes the rim of a cavity 66. Diametrically positioned within the cavity 66 are flanges 68a and 68b. Opposite shoulder 70 on barrel 60 is an end 64 which is engageable with the hollow 72 on button 74.

Referring to FIGS. 2 and 3, it can be appreciated that valving mechanism 90 is assembled and associated with housing 20 in the following manner. Barrel 60 is inserted into bore 54 of valve body 46 and this combination is inserted into well 76 of housing 20. End 64 is then snapped into engagement with the hollow 72 of button 74 to retain valve mechanism 90 in housing 20. Further, as seen in FIG. 2, valving mechanism 90 is disposed in housing 20 of the present invention for association with other elements of housing 20 in a manner to be subsequently discussed. Preferably, housing 20 is made of a polypropylene in a manner well known in the pertinent art.

By cross referencing FIG. 4 and FIG. 7, it can be appreciated that valve mechanism 90, when disposed within well 76 of housing 20, is free to reciprocate longitudinally along the axis of well 76 and to rotate about the longitudinal axis of well 76. During such movement, surface 52 of valve body 46 remains in fluid sealing engagement with the surface 78 of well 76. As will be appreciated by the skilled artisan, the integrity of fluid flow through cassette 10 is maintained by the fluid sealing engagement between surface 52 of valve body 46 and surface 78 of well 76 regardless whether valve mechanism 90 is mobile or stationary. Though this sealing engagement alone is normally sufficient to provide a bacterial seal for the fluid flow, as seen in FIGS. 4 and 7, cover 82 may also be associated with button 74 and housing 20 in a manner well known in the pertinent art to provide additional protection to the fluid paths through cassette 10.

As seen in FIG. 4 and FIG. 5, valve body 46 is positioned in well 76 with partial groove 50 aligned for fluid communication between the inlet 16 and pump port 38 of housing 20 through partial groove 50. In FIG. 6, valve body 46 is shown in the same longitudinal position with respect to well 76 but it is rotated to bring partial groove 50 into alignment for fluid communication between pump port 38 and outlet 18 through the partial groove 50. As envisioned in the present invention, valve body 46 is reciprocally rotated between its position as shown in FIG. 5 and its position as shown in FIG. 6 to provide for fluid communication into and out of the pump chamber 22 via pump port 38 for the purposes of pumping I.V. fluid through the system. This is the normal mode of operation of the cassette 10 with a pump 100.

Referring now to FIG. 7, it will be appreciated that valve body 46 can be longitudinally displaced within the well 76 to align annular groove 48 with inlet 16 and outlet 18. This relocation of valve body 46 within the well 76 of housing 20 is accomplished by an urging against button 74. As will be readily appreciated, this can be done manually. By cross referencing FIG. 7 with FIG. 8, it can be further appreciated that with valve body 46 aligned in well 76 as is best shown in FIG. 7, annular groove 48 permits fluid communication simultaneously between inlet 16, outlet 18 and pump port 38 via a fluid pathway which is best seen in FIG. 8.

It should be further appreciated by the skilled artisan that the orientation of valve body 46 as shown in FIGS. 7 and 11 can only be accomplished when cassette 10 has been disengaged from pump 100. This is so because engagement of cassette 10 with pump 100 causes front plate 32 to urge against shoulder 70 of valve mechanism 90 and thereby urge valve body 46 into the position relative to well 76 of housing 20 as substantially shown in FIGS. 4 and 10. It is only when there is disengagement of cassette 10 from pump 100 that button 74 can be depressed to align valve body 46 with housing 20 as substantially shown in FIGS. 7 and 11 to permit fluid flow from inlet 16 directly to outlet 18 via a route such as is shown substantially in FIG. 8.

In an alternate embodiment of the present invention, the valving mechanism 90 is as substantially shown in FIG. 7. In all important aspects, the alternate embodiment is similar to the preferred embodiment with the principal exception that annular groove 48 has been eliminated. As best seen in FIG. 9, valve body 46 of the alternate embodiment is formed only with a partial groove 50. In lieu of annular groove 48, a space is formed between valve body 46 and a washer 80. As best seen in FIG. 9, washer 80 is disposed around button 74 for fluid sealing engagement with surface 78 when valving mechanism 90 is disposed in well 76. In the alternate embodiment, upon disengagement of cassette 10 from the pump 100, depression of the button 74 moves the partial groove 50 out of alignment with pump port 38 and inlet 16 or outlet 18 and displaces valve body 46 into the position shown in FIG. 11. With valve body 46 in this position, fluid is allowed to flow around valve body 46 and into well 76 of housing 20 for direct fluid communication through the well 76 from inlet 16 to outlet 18.

OPERATION

In its operation, cassette 10 of the present invention is engaged with a pump 100 in a manner which brings connector 26 into engagement with shuttle 42. Further, housing 20 is positioned against pump case 34 in a manner which causes front plate 32 to urge against shoulder 70 and thereby position valve body 46 within the well 76 of housing 20 to align partial groove 50 with pump port 38. Engagement of cassette 10 with pump 100 also causes valve body actuator 36 to engage with the cavity 66 and flanges 68a and b therein for rotational operation of the valve body 46.

When cassette 10 and pump 100 are engaged, valve body 46 is firmly held in a longitudinal position within well 76 for normal pumping operations of the cassette 10 in cooperation with the pump 100. For such operations, stepper motor 44 drives shuttle 42 and piston 24 in a coordinated movement with the rotation of valve body 46 to provide for the intake of fluid from fluid source 12 into pump chamber 22 and the pumping of fluid from pump chamber 22 through outlet 18 to the patient 30.

Upon disengagement of cassette 10 from pump 100, button 74 can be actuated to cause longitudinal movement of valve body 46 within the housing 20 to align annular groove 48 with inlet 16, outlet 18 and pump port 38 in a manner that allows the simultaneous flow of fluid between inlet 16, outlet 18 and pump port 38. Upon reengagement of cassette 10 with pump 100 in a manner as described above, valve body 46 is repositioned within well 76 of housing 20 to permit further normal pumping operation of the cassette 10 in conjunction with pump 100.

While the particular gravity flow cassette as herein shown and disclosed in detail is fully capable of obtaining the objects and providing the advantage herein before stated, it is to be understood that it is merely illustrative of the presently preferred embodiment of the invention and that no limitations are intended to the details of construction or design herein shown other than as defined in the appended claims.

We claim:

1. A disposable cassette used with an I.V. infusion pump which comprises:

a pump chamber having a fluid inlet and a fluid outlet; and a valve body formed with a first fluid pathway and a separate second fluid pathway, said valve body normally disposed in said cassette for operative association with the pump chamber to alternatingly establish fluid communication through said first pathway from said inlet to said pump chamber and from said pump chamber to said outlet, said valve body means being movable longitudinally and axially in said cassette when said cassette is removed from the pump to establish fluid communication through said second fluid pathway simultaneously between said inlet, said outlet and said pump chamber.

2. A cassette as cited in claim 1 wherein said valve body is cylindrical and said cassette comprises a housing having a cylindrical well for slidably receiving said valve body therein to alternately establish fluid communication through said first fluid pathway and said second fluid pathway according to the position of said valve body in said well.

3. A cassette as cited in claim 2 wherein said first fluid pathway is a peripheral arcuate groove on the surface of said valve body.

4. A cassette as cited in claim 2 wherein said second fluid pathway is an annular groove on the surface of said valve body.

5. A cassette as cited in claim 3 wherein said second fluid pathway is an annular groove on the surface of said valve body.

6. A cassette as cited in claim 2 wherein said housing is made of polypropylene.

7. A cassette as cited in claim 2 wherein said valve body is made of urethane rubber.

8. A cassette for use with an I.V. infusion pump comprising:

a housing formed with a well and having an inlet, an outlet, and a pump port in fluid communication with said well;

a cylindrical shaped valve body means, formed with a circumferential annular groove on the surface thereof and a partial groove axially spaced from and substantially parallel to said annular groove, said valve body means slidably disposed in said well in fluid sealing engagement between the surface of said valve body means and the surface of said well for movement between a first position and a second position; and means for engaging said cassette with the pump to fix said valve body means in the first position wherein said partial groove is aligned with said pump port and said valve body means can be rotated in said well to alternately define a fluid path between said pump port and either said inlet or said outlet through said partial groove, said valve body means being longitudinally and axially moveable into the second position when said cassette is disengaged from the pump to align said annular groove with said inlet and simultaneously with said outlet and said pump port to allow for the free flow of fluid therebetween through said annular groove.

9. A cassette as cited in claim 8 wherein said valve body is made of urethane rubber.

10. A cassette as cited in claim 9 wherein said housing is made of polypropylene.

11. A cassette for use with an I.V. infusion pump comprising:

a infusion pump, a housing formed with a well and having an inlet, an outlet and a pump port in fluid communication with said well;

a cylindrical shaped valve body means disposed in said well for fluid sealing engagement between the surface of said valve body means and the surface of said well, said valve body further comprising an annular groove surrounding said valve body and a partial groove substantially parallel to said annular groove and axially spaced therefrom;

means for engaging said cassette with the pump to align said partial groove for fluid communication with said pump port; and means connectable with said valve body for rotating said valve body in said well to provide for fluid communication between said pump port and either said inlet or said outlet through said partial groove, said valve body means being relocateable in said well when said cassette is removed from said pump to align said annular groove with said inlet, said outlet and said pump port for fluid communication therebetween through said annular groove.

12. A cassette as cited in claim 11 wherein said valve body is made of urethane rubber.

13. A cassette as cited in claim 12 wherein said housing is made of polypropylene.

14. A disposable pump chamber cassette used with an I.V. infusion pump which comprises:

a housing having a well with an inlet, an outlet and a pump port in fluid communication therewith;

a valve body formed with an arcuate groove and an annular groove on the exterior surface of said valve body, said valve body slidably disposed in said well for movement between a first position and a second position; and means for holding said valve body in said first position during operative engagement of said cassette with the pump to alternately define a fluid pathway along said arcuate groove between said inlet and said pump port and between said pump port and said outlet, said valve body being moveable longitudinally and axially into said second position when said cassette is disengaged from said pump to permit fluid flow directly from said inlet to said outlet through said annular groove.

15. A cassette as cited in claim 14 wherein said valve body and said well are of a conforming cylindrical shape.

16. A cassette as cited in claim 15 wherein said housing is made of polypropylene.

17. A cassette as cited in claim 16 wherein said valve body is made of urethane rubber.

* * * * *